United States Patent [19]
Yamamoto et al.

[11] Patent Number: 5,223,616
[45] Date of Patent: Jun. 29, 1993

[54] HETEROCYCLIC DISPERSE DYE COMPOUND, THEIR PRODUCTION AND THEIR USE FOR DYEING OR PRINTING OF HYDROPHOBIC FIBERS

[75] Inventors: Jun Yamamoto; Junichi Sekihachi; Yosuke Yamamoto; Kazuhiro Machiguchi, all of Osaka; Yutaka Kayane, Nara, all of Japan

[73] Assignee: Sumitomo Chemical Company, Ltd., Osaka, Japan

[21] Appl. No.: 787,145

[22] Filed: Nov. 4, 1991

[30] Foreign Application Priority Data

Nov. 9, 1990 [JP] Japan ................... 2-304652

[51] Int. Cl.$^5$ ............... C07D 413/00; C07D 493/04; C07D 487/04; C07D 495/04; C07D 491/48
[52] U.S. Cl. ................. 544/153; 540/524; 544/111; 544/378; 546/167; 546/197; 548/127; 548/128; 548/129; 548/130; 548/131; 548/132; 548/133; 548/134; 548/135; 548/136; 548/138; 548/139; 548/141; 548/142; 548/143; 548/144; 548/145; 548/146; 548/152; 548/159; 548/182; 548/184; 548/186; 548/187; 548/189; 548/190; 548/202; 548/205; 548/206; 548/207; 548/213; 548/214; 548/215; 548/216; 548/217; 548/221; 548/225; 548/229; 548/230; 548/240; 548/241; 548/243; 548/245; 548/248; 548/255; 548/256; 548/262.2; 548/266.4; 548/463; 548/525; 548/530; 548/541; 548/557; 548/311.7; 548/305.1; 548/364.4; 549/60; 549/299; 549/414
[58] Field of Search ............ 549/299, 60, 414; 540/524; 544/153, 378, 111, 153, 378; 546/197, 167; 548/127-136, 138, 139, 141-146, 152, 159, 182, 184, 186, 187, 189, 190, 202, 206, 207, 213-217, 225, 229, 230, 233, 240, 241, 243, 245, 248, 255, 256, 262.2, 266.4, 300, 302, 327, 336, 356, 371, 374, 463, 530, 541, 557

[56] References Cited

U.S. PATENT DOCUMENTS

4,115,404  9/1978  Greenhaigh et al. ............ 8/1

FOREIGN PATENT DOCUMENTS

0146269  6/1985  European Pat. Off. .
0363034  4/1990  European Pat. Off. .
371223   6/1990  European Pat. Off. .
0397170  11/1990 European Pat. Off. .
2068402  8/1961  United Kingdom .

OTHER PUBLICATIONS

90 Chemical abstracts 7330w (1979).

*Primary Examiner*—Cecilia Tsang
*Attorney, Agent, or Firm*—Cushman, Darby & Cushman

[57] ABSTRACT

A heterocyclic compound which is useful for dyeing or printing hydrophobic fiber materials and which has the following formula (I),

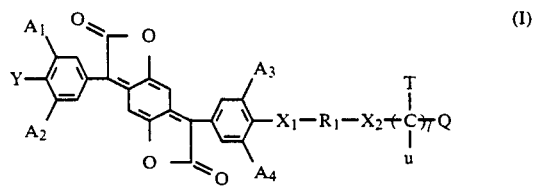

wherein $A_1$, $A_2$, $A_3$ and $A_4$ are each hydrogen, halogen, alkyl, alkoxy or alkenyl, $X_1$ is —O— or the like, $R_1$ is a methylene or the like, $X_2$ is a direct linkage or a divalent group of —O—, —S—, —SO—, —SO$_2$—,

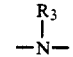

in which $R_3$ is a hydrogen atom or a $C_{1-4}$ alkyl group,

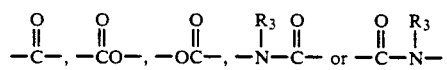

in which $R_3$ is as defined above, T and u are each independently hydrogen or a $C_{1-4}$ alkyl, l is 0 or an integer of 1 to 3, Q is an unsubstituted or substituted 5-, 6- or 7-membered saturated or unsaturated heterocyclic residue, Y is hydrogen, $C_{1-4}$ alkyl, a $C_{1-4}$ alkoxy group or the like.

5 Claims, No Drawings

HETEROCYCLIC DISPERSE DYE COMPOUND, THEIR PRODUCTION AND THEIR USE FOR DYEING OR PRINTING OF HYDROPHOBIC FIBERS

The present invention relates to heterocyclic compounds, their production and a process for dyeing or printing hydrophobic fiber materials therewith. More particularly, the present invention relates to benzodifuranone compounds useful for dyeing or printing hydrophobic fiber materials, for example, those such as polyester fibers and fiber materials containing the same, in a blue color.

Disperse dyes useful for dyeing or printing hydrophobic fiber materials have been increasingly desired to have much superior dyeability and capability of giving dyed or printed products excellent in various fastness properties with consumers' trend toward higher grade clothings. Answering such trend to increase the added value of dyed or printed products of hydrophobic fibers or hydrophobic fiber containing fiber materials, they are often subjected to various after-finish treatments such as softening finish, antistatic finish, feel-improving finish and the like. However, these after-finish treatments usually carried out at relatively high temperatures encounter problems of dye bleed, so that the dyed or printed products deteriorate in their wet fastness properties, particularly those such as washing fastness.

So far, many attempts to develop a blue disperse dye capable of giving dyed or printed products excellent in washing fastness have been directed mainly toward azo compounds, so that many azo compounds have been proposed therefor. However, those known azo compounds are not yet sufficient to solve the problem such that the washing fastness of dyed or printed products becomes markedly poor after the finish treatments.

There are other attempts to develop benzodifuranone compounds useful for dyeing or printing hydrophobic fiber materials, as disclosed in, for example, JP-A-52-109526 and 2-151663. However, the benzodifuranone compounds are also insufficient to satisfy both the dyeability and the fastness properties at the same time, and still awaiting for improvements.

It is the object of the present invention to provide disperse dye compounds having excellent dye properties for dyeing or printing hydrophobic fiber materials, particularly those such as polyester fiber materials, and capable of giving dyed or printed products bright in color and excellent in fastness properties such as light fastness, sublimation fastness and wet fastness, particularly those such as washing fastness.

The present invention provides heterocyclic compounds of the following formula (I),

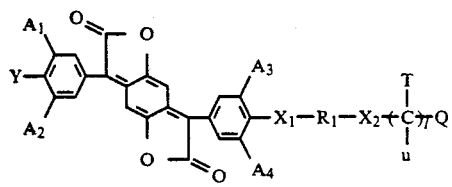
(I)

wherein $A_1$, $A_2$, $A_3$ and $A_4$ are each independently a hydrogen atom, a halogen atom or an unsubstituted or substituted alkyl, alkoxy or alkenyl group, $X_1$ is —O— or

(in which $R_2$ is a hydrogen atom or an unsubstituted or substituted alkyl, alkenyl, cycloalkyl, aryl or aralkyl group and $R_2$ may link to $A_3$ or $A_4$ to form a heterocyclic ring), $R_1$ is a methylene group or a straight or branched $C_{2-6}$ alkylene group unsubstituted or substituted by a hydroxy group, a $C_{1-4}$ alkoxy group or a $C_{1-4}$ alkylcarbonyloxy group, $X_2$ is a direct linkage or a divalent group of —O—, —S—, —SO—, —SO$_2$—,

(in which $R_3$ is a hydrogen atom or a $C_{1-4}$ alkyl group),

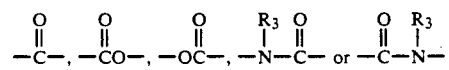

(in which $R_3$ is as defined above), T and u are each independently a hydrogen atom or a $C_{1-4}$ alkyl group, l is 0 or an integer of 1 to 3, Q is an unsubstituted or substituted 5-, 6- or 7-membered saturated or unsaturated heterocyclic residue, Y is a hydrogen atom, a $C_{1-4}$ alkyl group, a $C_{1-4}$ alkoxy group, a group of the formula, $$-X_3-R_1-X_2\!-\!(C)_{\overline{l}}Q, \quad (i)$$

in which $R_1$, $X_2$, T, u, Q and l
as defined above, and $X_3$ is

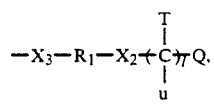

in which $R_4$ is a hydrogen atom or an unsubstituted or substituted alkyl, alkenyl, cycloalkyl, aryl or aralkyl group and $R_4$ may link to $A_1$ or $A_2$ to form a hetrocyclic ring, provided that the group of the formula (i) as Y is the same as or different from the group of the formula (i) appended to $X_1$, a group of the formula

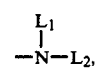
(ii)

in which $L_1$ and $L_2$ are each independently a hydrogen atom or an unsubstituted or substituted alkyl, alkenyl, cycloalkyl, aryl or aralkyl group and one of $L_1$ and $L_2$ may link to $A_1$ or $A_2$ to form heterocyclic ring, or a group of the formula

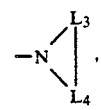
(iii)

in which $L_3$ and $L_4$ are each independently an alkylene group, an alkenylene group or a $C_{1-4}$ alkylcarbonyl group, or a group of the formula

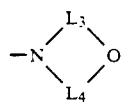

in which $L_3$ and $L_4$ are as defined above, and Y may link to $A_1$ or $A_2$ to form —OCH$_2$O—, with a proviso that when X is —o—, Y is

in which $L_1$ and $L_2$ are as defined above,

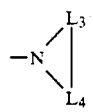

in which $L_3$ and $L_4$ are as defined above,

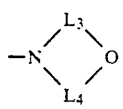

in which $L_3$ and $L_4$ are as defined above,

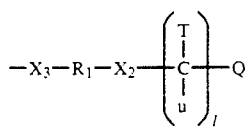

in which $X_3$, $R_1$, $X_2$, T, u, l and Q are as defined above,

The present invention also provides a process for producing the heterocyclic compounds of the formula (I).

The heterocyclic compounds of the formula (I) can be produced, for example, by the following processes.

That is, a tartronic acid compound of the following formula (II) a,

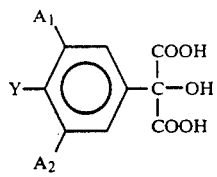

wherein $A_1$, $A_2$ and Y are as defined above, is reacted with a compound of the following formula (III)a;

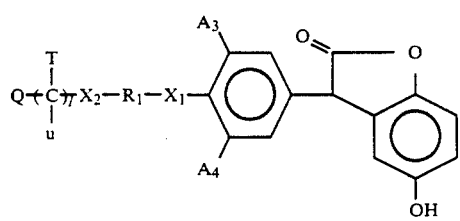

wherein Q, T, u, $X_2$, $R_1$, $X_1$, l, $A_3$ and $A_4$ are as defined above, at 50°–200° C. without solvent or in an acidic medium such as acetic acid and then the reaction product is oxidized with an oxidant to obtain the heterocyclic compound.

Alternatively, a tartronic acid compound of the following formula (II)b,

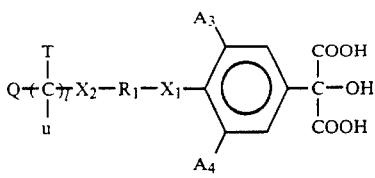

wherein Q, T, u, l, $X_2$, $R_1$, $X_1$, $A_3$ and $A_4$ are as defined above, is reacted with a compound of the following formula (III)b,

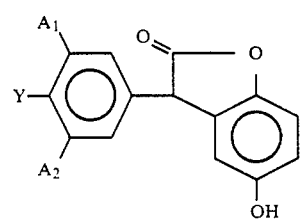

wherein Y, $A_1$ and $A_2$ are as defined above, at 50°–200° C. without solvent or in an acidic medium such as acetic acid and the reaction product is oxidized with an oxidant.

The present invention further provides a process for dyeing or printing hydrophobic fiber materials, which comprises contacting the fiber materials with the heterocyclic compound of the formula (I).

The unsaturated heterocyclic residue represented by Q includes those represented by the following formulas.

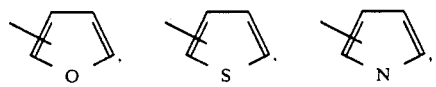

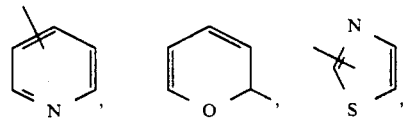

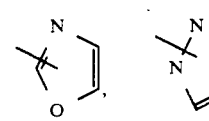
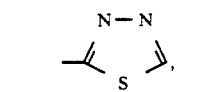

The saturated heterocyclic residue represented by Q includes those represented by the following formulas.

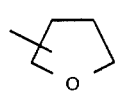 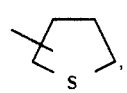 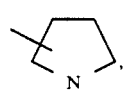

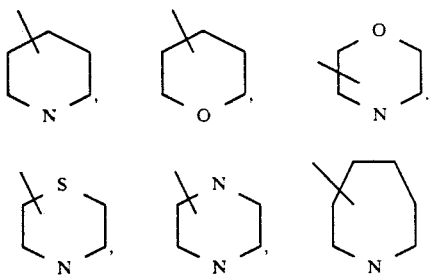

Furthermore, the heterocyclic residue represented by Q may be condensed with benzene or heterocyclic ring to form those exemplified below.

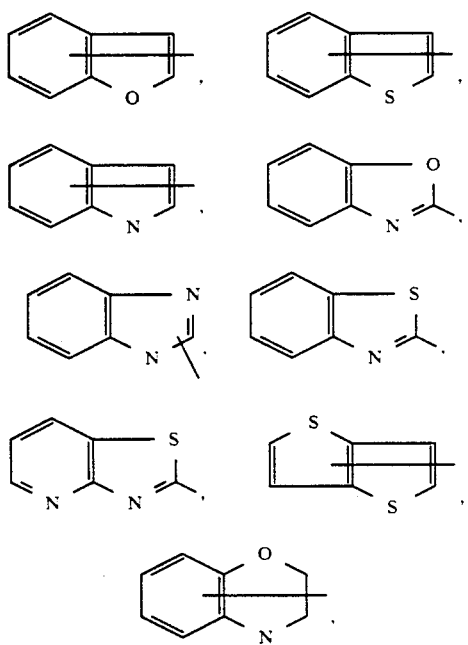

These heterocyclic residues are unsubstituted or substituted once or twice by halogen such as fluorine, chlorine or bromine, hydroxy, $C_{1-4}$ alkyl, $C_{1-4}$ alkoxy, $C_{1-4}$ alkylcarbonyl, $C_{1-4}$ alkoxycarbonyl, cyano, keto, or primary, secondary or tertiary amino unsubstituted or substitured by an alkyl group having 1 to 4 carbon atoms.

The keto group means those formed by bonding the heterocyclic ring-constituting carbon atom and an oxygen atom through a double bond, such as those exemplified below.

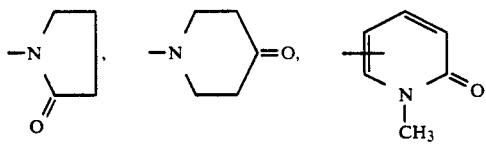

The unsubstituted or substituted alkyl groups represented by $A_1$, $A_2$, $A_3$, $A_4$, $R_2$, $R_4$, $L_1$ and $L_2$ are $C_{1-4}$ alkyl groups and the substitutent includes, for example, $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino and $C_{1-4}$ alkylcarbonylamino groups.

The unsubstituted or substituted alkoxy groups represented by $A_1$, $A_2$, $A_3$, and $A_4$ are $C_{1-4}$ alkoxy groups and the substituent includes, for example, $C_{1-4}$ alkyl, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino and $C_{1-4}$ alkylcarbonylamino groups.

The unsubstituted or substituted alkenyl groups represented by $A_1$, $A_2$, $A_3$, $A_4$, $R_2$, $R_4$, $L_1$ and $L_2$ are $C_{1-4}$ alkenyl groups and the substitutent includes, for example, $C_{1-4}$ alkyl, $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino and $C_{1-4}$ alkylcarbonylamino groups.

When $R_2$, $R_4$, $L_1$ and $L_2$ are substituted cycloalkyl, aryl or aralkyl groups, the substituents include, for example, $C_{1-4}$ alkyl, $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino and $C_{1-4}$ alkylcarbonylamino groups.

The compounds of the formula (I) are useful for dyeing or printing hydrophobic fiber materials, particularly those such as polyester fiber matereils. In utilizing the present heterocyclic compound in such field, the compounds (I) can be finely pulverized in an aqueous medium together with a suitable dispersant such as naphthalenesulfonic acid/formaldehyde condensate, lignin sulfonic acid or the like, thereby obtaining a liquid dye dispersion. The liquid dye dispersion can be used as it is for the dyeing or printing of fiber materials, or dried with, for example, a spray drier to be made in a powder form.

Dyeing can be carried out by a high temperature dyeing method wherein hydrophobic fiber materials are dipped in an aqueous dye bath and heated to a temperature of 105° C. or higher, preferably 110° to 140° C. under increased pressures, a carrier dyeing method wherein dyeing is carried out in the presence of a carrier such as o-phenylphenol, trichlorobenzene or the like at a relatively high temperature, for example, water-boiling temperature, or a thermosol method wherein the fiber materials are padded with an aqueous dye dispersion and dry-heated at a temperature of 150° to 230° C. for 30 to 60 seconds.

Printing can be carried out by mixing the aqueous dye dispersion with a suitable stock paste to obtain a color paste, padding fiber materials with the color paste and then steaming or thermosol-treatment.

In addition, the fiber materials can also be dyed by a solvent dyeing method wherein an organic solvent such as trichloroethylene, perchloroethylene or the like is used as a dyeing medium. The dyed or printed products thus obtained can be subjected, if desired, to after-finish treatments such as softening finish, water-repelling finish, feel-improving finish, antistatic finish and sanitary finish in a conventional manner. The various fastness properties, especially washing fastness do not deteriorate even after the after-finish treatments.

The present heterocyclic compounds of the formula (I) can be characterized by the facts such that hydrophobic fiber materials, particularly those such as polyester fiber materials, can be dyed or printed in a usual manner using the present compound (I), thereby obtaining dyed or printed products of a brilliant blue color excellent in various fastness properties such as light fastness, sublimation fastness and wet fastness and such fastness properties do not deteriorate even after heat-set treatment and after-finish treatments.

The present heterocyclic compounds of the formula (I) can be characterized also by superior dyeability, so that dyed or printed products of a deep color without unevenness of dyeing can be readily obtained, with superior build-up property and superior dye bath stability (low pH sensitivity).

In consideration of the characteristic features described above, the heterocyclic compounds of the present invention can be advantageously used particularly for the dyeing of apparels such as sportswear, which are required to be dyed usually in a deep color and to have superior washing fastness because they are to be washed again and again. Moreover, a compound of the present invention can be used in combination with other dyes to improve the dye performance and to obtain a variety of color.

The present invention is illustrated in more detail with reference to the following Examples, which are only illustrative but not limitative for the scope of the present invention. In the Examples, part and % are by weight.

EXAMPLE 1

A mixture of 4-tetrahydrofurfuryloxyphenyltartronic acid (3.27 parts) and 5-hydroxy-2-oxo-3-(4-acetylamnophenyl)-2,3-dihydrobenzofuran (2.84 parts) was kept at 80° C. for 6 hours in a mixed solvent of acetic acid (38 parts) and concentrated sulfuric acid (2 parts), and thereafter, ammonium persulfate (2.34 parts) was added to the reaction mixture, followed by heating for additional 1 hour. The reaction mixture was cooled to room temperatue and thereafter, mixed with methanol (50 parts). The resulting crystals were collected on a filter, washed with water, and then mixed with 78% sulfuric acid (100 parts). The mixture was heated at 95° C. for 5 hours, cooled and then discharged into water (1000 parts). The resulting crystals were collected on a filter, washed with water and dried to obtain a compound of the following formula (1).

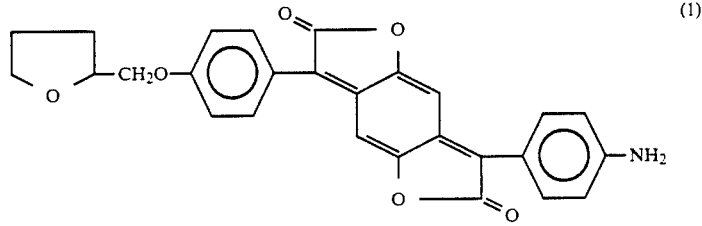

The compound was dissolved in DMF to obtain a solution of medium blue color.

EXAMPLE 2

The compound of the formula (1) (1.0 part) was finely pulverized in an aqueous medium with the aid of naphthalenesulfonic acid-formaldehyde condensate (3.0 parts). The resulting dye dispersion was dried to form powder. Polyester cloth (10 parts, Tetron jersey, a product of Teijin Limited, in Japan) was dipped in a dyebath containing the powder (0.6 part), and dyeing was carried out for 60 minutes at 130° to 135° C. under increased pressures. The dyed cloth was subjected to reduction-rinsing treatment at 85° C. for 10 minutes in a solution of sodium hydroxide (3 parts), hydrosulfite (3 parts) and a betaine amphoteric surfactant (3 parts) in water (3000 parts), washed with water and then dried, thereby obtaining a dyed product of a brilliant blue color superior in light fastness, sublimation fastness and wet fastness.

The resulting dyed product was subjected to softening and anti-static finishing by the following method.

The dyed product was dipped in a padding liquor containing a soft-finishing agent (10 g/l, Sumitex Softener LK-1, a product of Sumitomo Chemical Co., Ltd., in Japan) and an anti-static agent (5 g/l, Sumistat F-1, a product of Sumitomo Chemical Co., Ltd., in Japan), squeezed uniformly at a pick-up of 80%, again dipped in the same padding liquor as above, squeezed at the same level as above, pre-dried at 80° C. for 2 minutes and then subjected to heat set at 170° C. for 1 minute.

The thus after-finished dyed product was found to have a superior washing fastness.

EXAMPLE 3

The compound of the formula (I) obtained in Example 1 (1.3 part) was finely pulverized with the aid of lignin sulfonic acid (3.7 parts). To the resulting dispersion were added hot water (35 parts) and a half emulsion paste (60 parts) having the following composition.

| | |
|---|---|
| O/W Emulsion | 300 parts |
| Stock paste (12% Maypro gum NP) | 694 parts |
| Sodium chlorate | 4 parts |
| Tartaric acid | 2 parts |

-continued

Total 1.000 parts

Polyester cloth (Tetron tropical, a product of Teijin Limited, in Japan) was printed with the above obtained printing paste, dried and steamed for 7 minutes at 170° C. under atmospheric pressure by a high temperature steamer. The printed cloth was subjected to reduction rinsing treatment, washing with water, drying, and softening and anti-static finishings in this order in a manner similar to that of Example 1. The resulting printed product of a blue color was found to have superior light, sublimation and wet fastness properties, particularly washing fastness.

EXAMPLE 4

A mixture of 5-hydroxy-2-oxo-3-(4-acetylamnophenyl)-2,3-dihydrobenzofuran (2.84 parts), 4-N-(tetrahydropyra-2-nylmethyl)-3-methylphenyltartronic acid (3.24 parts) and acetic acid (50 parts) was heated at 100° C. for 6 hours and thereafter, ammonium persulfate (2.34 parts) was added to the reaction mixture. The resulting mixture was kept at 100° C. for additional 1 hour. The reaction mixture was cooled to room temperature and thereafter, the procedure of Example 1 was repeated to obtain a compound of the following formula (2).

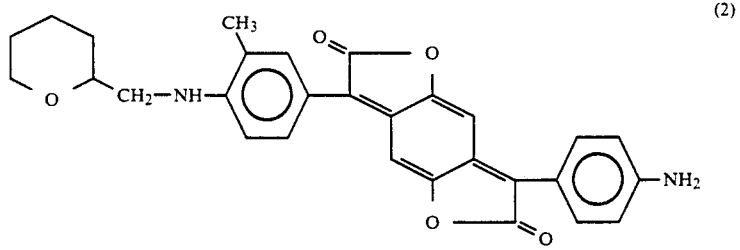

(2)

The solution of this compound in DMF had a greenish blue color.

Using the compound, Example 2 was repeated to obtain a dyed product superior in light, sublimation and wet fastness properties, particularly superior in washing fastness.

EXAMPLES 5 TO 30

In a manner similar to that of Example 4, the compounds as shown in the following Table 1 were prepared. These compounds can be used for dyeing polyester cloth to obtain dyed product having blue color and having superior washing fastness.

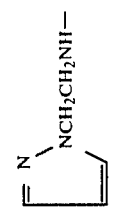

-continued

| No. | A1 | Y | A3 | X1 | R1 | X2 | Q |
|---|---|---|---|---|---|---|---|
| 11 | H | CH₃CH₂CHNH— (with CH₃ branch) | H | —NH— | —CH₂— | " | tetrahydrofuran with 2,5-CH₃ groups |
| 12 | CH₃CH₂— | H₂N— | H | —NH— | —CH₂CH₂— | " | tetrahydrothiophene (2-methyl) |
| 13 | (CH₃)₂CHO— | H₂N— | H | —O— | —CH₂CH₂CH₂— | —C(=O)— | N-methylpyrrolidine |
| 14 | H | morpholino (N-linked) | H | —O— | —(CH₂)₄— | Direct linkage | morpholine |
| 15 | — | —CH₂CH₂CH₂NH— | H | O | —CH₂— | Direct linkage | N-ethyl pyrrolidine (with CH₂CH₃) |
| 16 | CH₃O— | H₂N— | H | —NH— | —CH₂CH₂— | " | N-methyl piperidine (3-methyl) |

-continued

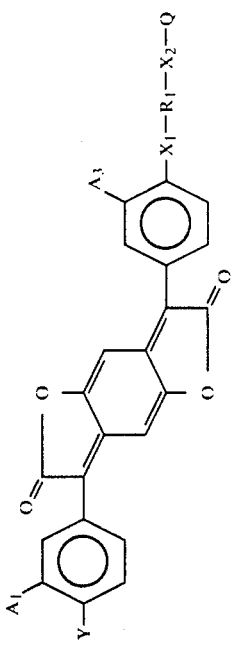

| No. | $A_1$ | Y | $A_3$ | $X_1$ | $R_1$ | $X_2$ | Q |
|---|---|---|---|---|---|---|---|
| 17 | H | $H_2N-$ | H | $-NH-$ | $-CH_2CHCH_2-$<br>$\|$<br>OH | " | ![lactam ring with N-C=O] |
| 18 | $CH_3$ | $CH_3COCH_2CH_2NH-$<br>$\|\|$<br>O | H | $-NH-$ | $-CH_2CH_2-$ | " | ![4-chloropiperidine N-linked] |
| 19 | $CH_3O-$ | $CH_3O-$ | H | $-NH-$ | $-CH_2CHCH_2-$<br>$\|$<br>$OCCH_3$<br>$\|\|$<br>$O$ | " | ![piperazine N—$C_4H_9$-n] |
| 20 | $CH_3CH_2CH_2-$ | $H_2N-$ | H | O | $-CH_2-$ | " | ![furan with $COC_2H_5$] |
| 21 | | $-OCH_2CH_2O-$ | $CH_3$ | $-NH-$ | $-CH_2CH_2-$ | " | ![thiophene with $CH_3$ groups] |
| 22 | Cl | $CH_3CH_2NH-$ | H | $-NH-$ | $-CH_2-$ | $-OC-$<br>$\|\|$<br>$O$<br>Direct linkage | ![thiazole ring] |

-continued

| No. | A₁ | Y | A₃ | X₁ | R₁ | X₂ | Q | Formula |
|---|---|---|---|---|---|---|---|---|
| 23 | H | (CH₃)₂N— | H | —O— | —CH₂CH₂— | —O— | 2-methylbenzothiazole with Cl | |
| 24 | H | pyrrol-1-yl | H | —NH— | —CH₂CH₂— | —O— | N-methylindole | |
| 25 | CH₃— | —NH₂ | H | —O— | —CH₂CH₂— | —S— | 2-methylbenzoxazole | |
| 26 | CH₃— | —NH₂ | H | —O— | —CH₂CH₂CH₂— | —SO₂— | 2-methylbenzoxazole | |
| 27 | CH₃ | NH₂ | H | —N(C₂H₅)— | —CH₂— | Direct linkage | 2-methyltetrahydrofuran | |
| 28 | H | " | —CH₂CH₂CH₂N⟨ | —CH₂CH₂CH₂N⟨ | | | " | |

-continued

| No. | $A_1$ | Y | $A_3$ | $X_1$ | $R_1$ | $X_2$ | Q |
|---|---|---|---|---|---|---|---|
| 29 | " | H | H | $-\underset{H}{N}-$ | $-CH_2CH_2CH_2-$ | $\underset{O}{\overset{O}{\underset{\|}{S}}}$ | benzothiazole |
| 30 | " | $\underset{O}{\text{tetrahydropyranyl-O-}}CH_2OCCH_2NH-$ | H | $-O-$ | $-CH_2-$ | Direct linkage | 2,5-dimethylthiophene |

Formula: structure with $A_1$-phenyl-Y and $A_3$-phenyl-$X_1$-$R_1$-$X_2$-Q substituents on central quinone-dione system.

EXAMPLES 31 TO 47

In a manner similar to that of Example 4, the compounds as shown in the following Table 2 were prepared. These compounds can be used for dyeing polyester cloth to obtain dyed product having superior washing fastness.

| NO. | A₁ | A₂ | A₃ | A₄ | Y | X₁ | R₁ | X₂ | i | T | u | Q |
|---|---|---|---|---|---|---|---|---|---|---|---|---|
| 31 | H | CH₃ | H | CH₃ | H₂N— | —NH— | —CH₂CH₂— | —O— | 1 | H | H | 2,5-dimethyl-tetrahydrofuran |
| 32 | CH₃ | CH₃ | H | H | H₂N— | —O— | —CH₂CH₂— | —O— | 1 | H | H | 2-methyl-tetrahydrofuran |
| 33 | CH₃ | H | CH₃ | H | H₂N— | —NH— | —CH₂CH₂— | —O−CO− | 1 | H | H | 2-methyl-tetrahydrofuran |
| 34 | H | CH₃ | Br | H | H₂N— | —O— | —CH₂CH₂CH₂— | —O— | 1 | H | H | tetrahydrofuran |
| 35 | CH₃ | H | H | H | CH₃CH₂NH— | —NH— | —CH₂CHCH₂— (CH₃) | —O— | 1 | CH₃ | CH₃ | 2-methyl-2,5-dihydrofuran |
| 36 | H | H | H | H | (CH₃CH₂)₂N— | —O— | —CH₂CH₂— | —S— | 3 | H | H | 2-methyl-2,3-dihydrofuran |
| 37 | CH₃ | H | H | H | H₂N— | —NH— | —CH₂CH₂— | —O−CO− | 2 | H | H | N-methylmorpholine |

-continued
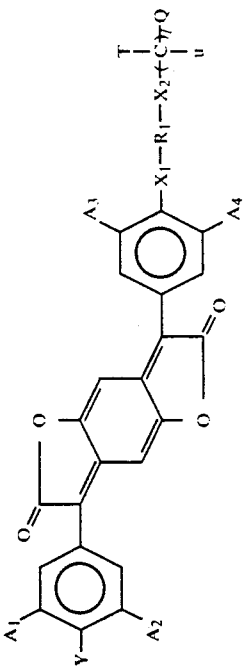
| NO. | A1 | A2 | A3 | A4 | Y | X1 | R1 | X2 | t | T | u | Q |
|---|---|---|---|---|---|---|---|---|---|---|---|---|
| 38 | H | CH₃ | H | CH₃ | CH₃CH₂CHNH— (with CH₃ branch) | —NH— | —CH₂CH₂— | —O— | 1 | H | H | pyrrolidine ring |
| 39 | H | CH₃ | H | H | H₂N— | —O— | —CH₂— | —CO— (=O) | 2 | H | H | pyrrolidinone ring |
| 40 | H | H | H | H | H₂N— | —NH— | —CH₂CH₂— | —O— | 2 | H | H | caprolactam ring |
| 41 | H | H | H | Cl | morpholine ring | —NH— | —CH₂CH₂— | O | 1 | H | H | thiophene ring |
| 42 | H | H | H | H | H₂N— | —O— | —CH₂CH₂CH₂— | —NC(=O)— | 2 | H | H | piperidine ring |
| 43 | CH₃ | H | H | CH₃ | H₂N— | —NH— | —CH₂CH₂— | —CN(=O)— | 2 | H | H | morpholine ring |

-continued
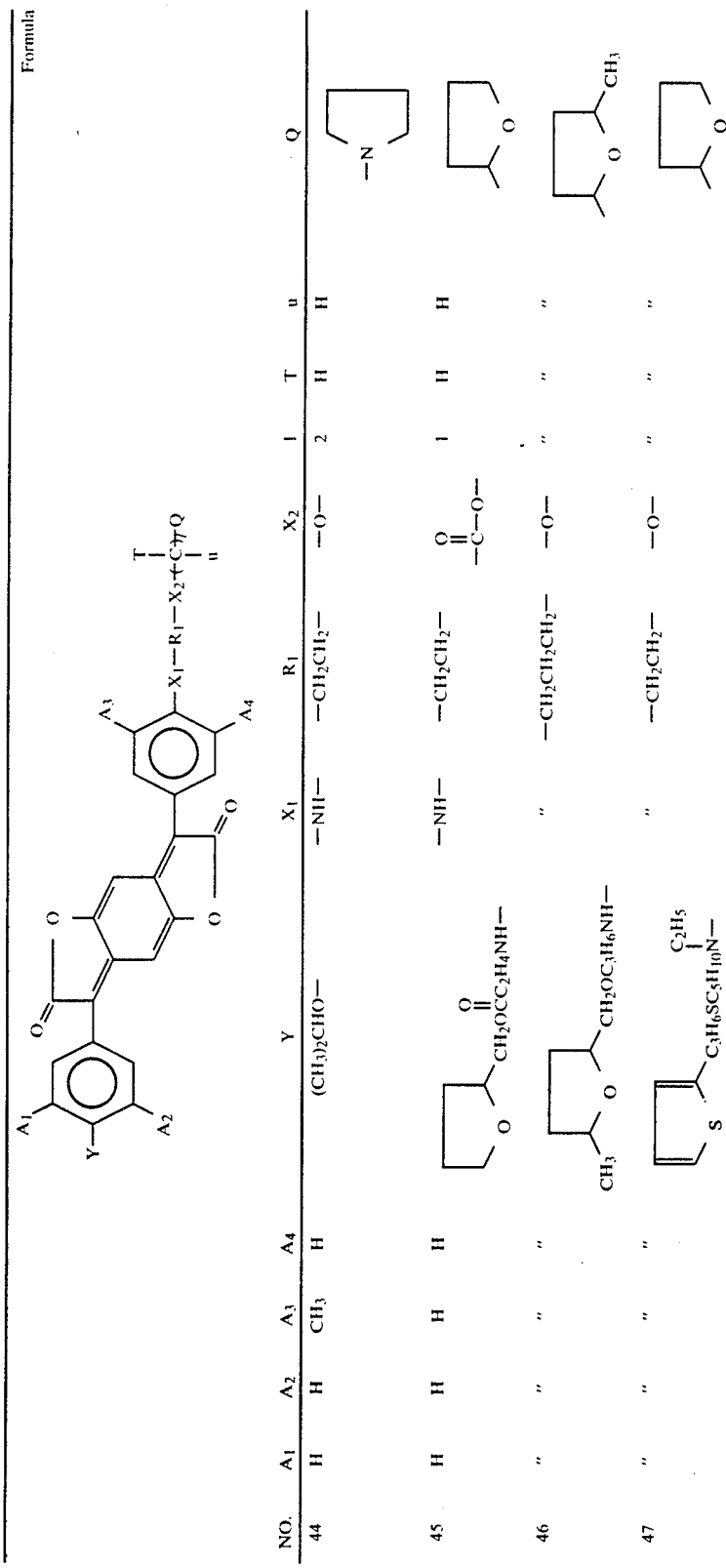
| NO. | A₁ | A₂ | A₃ | A₄ | Y | X₁ | R₁ | X₂ | l | T | u | Q |
|---|---|---|---|---|---|---|---|---|---|---|---|---|
| 44 | H | H | CH₃ | H | (CH₃)₂CHO— | —NH— | —CH₂CH₂— | —O— | 2 | H | H | [pyrrolidine ring with N] |
| 45 | H | H | H | H | [tetrahydrofuran-CH₂OCC₂H₄NH—, with C=O] | —NH— | —CH₂CH₂— | —O—C(=O)—O— | 1 | H | H | [tetrahydrofuran ring with O] |
| 46 | " | " | " | " | [tetrahydrofuran(CH₃)-CH₂OC₃H₆NH—] | " | —CH₂CH₂CH₂— | —O— | " | " | " | [tetrahydrofuran ring with O and CH₃] |
| 47 | " | " | " | " | [thiophene-C₂H₆SC₅H₁₀N— with C₂H₅] | " | —CH₂CH₂— | —O— | " | " | " | [tetrahydrofuran ring with O] |

We claim:
1. A heterocyclic compound of the following formula (I)

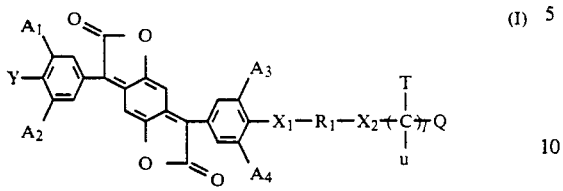

wherein
$A_1$, $A_2$, $A_3$ and $A_4$ are each and independently selected from the group consisting of a hydrogen atom, a halogen atom, a $C_{1-4}$ alkyl group unsubstituted or substituted by $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino or $C_{1-4}$ alkylcarbonylamino, a $C_{1-4}$ alkoxy group unsubstituted or substituted by $C_{1-4}$ alkyl, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino or $C_{1-4}$ alkylcarbonylamino, a $C_{2-4}$ alkenyl group unsubstituted or substituted by $C_{1-4}$ alkyl, $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino or $C_{1-4}$ alkylcarbonylamino;
$X_1$ is —O— or $R_2$—N< in which $R_2$ is selected from the group consisting of a hydrogen atom, a $C_{1-4}$ alkyl group unsubstituted or substituted by $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino or $C_{1-4}$ alkylcarbonylamino, a $C_{2-4}$ alkenyl group unsubstituted or substituted by $C_{1-4}$ alkyl, $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkoxycarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino or $C_{1-4}$ alkylcarbonylamino, and a $C_{4-7}$ cycloalkyl, $C_{6-10}$ aryl or $C_{7-9}$ aralkyl group which is unsubstituted or substituted by $C_{1-4}$ alkyl, $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino or $C_{1-4}$ alkylcarbonylamino, and wherein $R_2$ may link to $A_3$ or $A_4$ to form a 6-membered heterocyclic ring having a nitrogen atom;
$R_1$ is a methylene group or a straight or branched $C_{2-6}$ alkylene group unsubstituted or substituted by a hydroxy group, a $C_{1-4}$ alkoxy group or a $C_{1-4}$ alkylcarbonyloxy group;
$X_2$ is a direct linkage or a divalent group of —O—, —S—, —SO—, —SO$_2$—, $R_3$—N< in which $R_3$ is a hydrogen atom or a $C_{1-4}$ alkyl group,

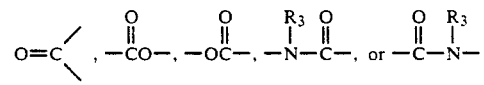

in which $R_3$ is as defined above;
T and u are each independently a hydrogen atom or a $C_{1-4}$ alkyl group;
l is 0 or an integer of 1, 2 or 3;
Q is a 5-, 6- or 7- membered saturated or unsaturated heterocyclic residue having from 1 to 3 hetero atoms, said hetero atom being selected from the group consisting of nitrogen, sulphur and oxygen, said heterocyclic residue being substituted or unsubstituted once or twice by halogen, hydroxy, $C_{1-4}$ alkyl, $C_{1-4}$ alkoxy, $C_{1-4}$ alkylcarbonyl, $C_{1-4}$ alkoxycarbonyl, cyano, keto or primary, secondary or tertiary amino unsubstituted or substituted by alkyl having from one to four carbon atoms, wherein said heterocyclic residue may be condensed with benzene or a 5- or 6- membered heterocyclic ring having one or two hetero atoms selected from the group consisting of nitrogen and sulphur;
Y is a hydrogen atom, a $C_{1-4}$ alkyl group, a $C_{1-4}$ alkoxy group, a group of the formula (i), a group of the formula (ii), a group of the formula (iii) or a group of the formula (iv), wherein formula (i) is

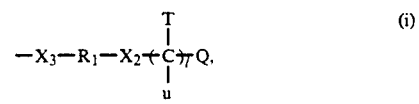

in which $R_1$, $X_2$, T, u, Q and l are as defined above, and $X_3$ is $R_4$—N< in which $R_4$ is selected from the group consisting of a hydrogen atom, a $C_{1-4}$ alkyl group unsubstituted or substituted by $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino or $C_{1-4}$ alkylcarbonylamino, a $C_{2-4}$ alkenyl group unsubstituted or substituted by $C_{1-4}$ alkyl, $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkylcarbonyloxy, $C_{1-4}$ alkoxycarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino or $C_{1-4}$ alkylcarbonylamino, and a $C_{4-7}$ cycloalkyl, $C_{6-10}$ aryl or $C_{7-9}$ aralkyl group which is unsubstituted or substituted by $C_{1-4}$ alkyl, $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino or $C_{1-4}$ alkylcarbonylamino, and wherein $R_4$ may link $A_1$ or $A_2$ to form a heterocyclic ring having a nitrogen atom; formula (ii) is

(ii)

in which $L_1$ and $L_2$ are each independently selected from the group consisting of a hydrogen atom, a $C_{1-4}$ alkyl group unsubstituted or substituted by $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino or $C_{1-4}$ alkylcarbonylamino, a $C_{2-4}$ alkenyl group unsubstituted or substituted by $C_{1-4}$ alkyl, $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkythio, $C_{1-4}$ alkylsulfinyl, $C_{1-4}$ alkysulfonyl, phenylsulfonyl, sulfamoyl, benzoyl, $C_{1-4}$ alkylamino, di $C_{1-4}$ alkylamino, N,N-di $C_{1-4}$ alkyl $C_{1-4}$ alkylamino, $C_{1-4}$ alkylsulfonylamino or $C_{1-4}$ alkylcarbonylamino, and a $C_{4-7}$ cycloalkyl, $C_{6-10}$ aryl or $C_{7-9}$ aralkyl group which is unsubstituted or substituted by $C_{1-4}$ alkyl, $C_{1-4}$ alkoxy, $C_{1-4}$ alkoxy $C_{1-4}$ alkyl, $C_{1-4}$ alkoxy $C_{1-4}$ alkoxy, $C_{1-4}$ alkylcarbonyl, $C_{1-4}$ alkoxycarbonyl, $C_{1-4}$ alkoxycarbonyloxy, $C_{1-4}$ alkylcarbonyloxy, $C_{1-4}$ alkoxy $C_{1-4}$ alkoxycarbonyloxy, $C_{1-4}$ alkoxy $C_{1-4}$ alkylcarbonyloxy, cyclohexyl, phenyl, diphenyl, nitro, hydroxy, cyano, halogen, carbamoyl, $C_{1-4}$ alkylthio, $C_{1-4}$ alkylsulfinyl, $C_{1-4}$ alkylsulfonyl, phenylsulfonyl, sulfamoyl,·benzoyl, $C_{1-4}$ alkylamino, di $C_{1-4}$ alkylamino, N,N,-di $C_{1-4}$ alkyl $C_{1-4}$ alkylamino, $C_{1-4}$ alkylsulfonylamino or $C_{1-4}$ alkylcarbonylamino; formula (iii) is

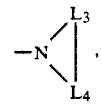
(iii)

in which $L_3$ and $L_4$ are each independently a $C_1$–$C_4$ alkylene group, a $C_{2-4}$ alkenylene group or a $C_{1-4}$ alkylcarbonyl group; formula (iv) is

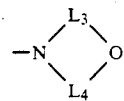
(iv)

in which $L_3$ and $L_4$ are as defined above,
with the independent provisos (a) Y may link to $A_1$ or $A_2$ to form $-OCH_2O-$; (b) that when $X_1$ is $-O-$, Y is

(ii)

in which $L_1$ and $L_2$ are as defined above,

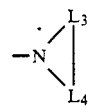
(iii)

in which $L_3$ and $L_4$ are as defined above,

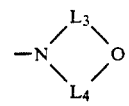
(iv)

in which $L_3$ and $L_4$ are as defined above, or

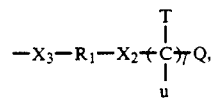
(i)

in which $R_1$, $X_3$, $X_2$, T, u, l and Q are as defined above; (c) that the group of the formula (i) as Y is the same as or different from the group of the formula (i) appended to $X_1$; and (d) one of $L_1$ and $L_2$ may link to $A_1$ or $A_2$ to form a heterocyclic ring having a nitrogen atom.

2. The compound according to claim 1, wherein Q is a 5-, 6- or 7-membered unsaturated heterocyclic residue unsubstituted or substituted once or twice by a halogen atom, a hydroxy group, a $C_{1-4}$ alkyl group, a $C_{1-4}$ alkoxy group, a $C_{1-4}$ alkylcarbonyl group, a $C_{1-4}$ alkoxycarbonyl group, a cyano group, a keto group, or a primary, secondary or tertiary amino group unsubstituted or substituted by an alkyl group having 1 to 4 carbon atoms.

3. The compound according to claim 2, wherein the unsaturated heterocyclic residue is furyl, thienyl, pyrrolyl, pyridyl, pyranyl, thiazolyl, oxazolyl, pyrazolyl, imidazolyl, thiadiazolyl, s-triazinyl, benzofuranyl, benzothienyl, indolyl, benzoxazolyl, benzimidazolyl or benzothiazolyl.

4. The compound according to claim 1, wherein Q is a 5-, 6- or 7-membered saturated heterocyclic residue unsubstituted or substituted once or twice by a halogen atom, a hydroxy group, a $C_{1-4}$ alkyl group, a $C_{1-4}$ alkoxy group, a $C_{1-4}$ alkylcarbonyl group, a $C_{1-4}$ alkoxycarbonyl group, a cyano group, a keto group, or a primary, secondary or tertiary amino group unsubstituted or substituted by an alkyl group having 1 to 4 carbon atoms.

5. The compound according to claim 4, wherein the saturated heterocyclic residue is tetrahydrofuryl, tetrahydrothienyl, tetrahydropyranyl, pyrrolidyl, piperidyl, piperazinyl, morpholinyl or hexahydroazepinyl.

* * * * *